US 8,857,241 B2

(12) United States Patent
Nakashima (10) Patent No.: US 8,857,241 B2
(45) Date of Patent: Oct. 14, 2014

(54) GAS SENSOR

(75) Inventor: Takashi Nakashima, Inuyama (JP)

(73) Assignee: NGK Spark Plug Co., Ltd., Aichi (JP)

( * ) Notice: Subject to any disclaimer, the term of this patent is extended or adjusted under 35 U.S.C. 154(b) by 130 days.

(21) Appl. No.: 13/288,896

(22) Filed: Nov. 3, 2011

(65) Prior Publication Data

US 2012/0111092 A1    May 10, 2012

(30) Foreign Application Priority Data

Nov. 10, 2010  (JP) .................................. 2010-252266
Sep. 20, 2011  (JP) .................................. 2011-204323

(51) Int. Cl.
*G01N 7/10*    (2006.01)
*G01N 27/407*  (2006.01)

(52) U.S. Cl.
CPC .................................. *G01N 27/4077* (2013.01)
USPC .......... 73/23.31; 204/424; 204/426; 204/428; 73/114.69; 73/114.71; 73/114.72

(58) Field of Classification Search
CPC .......... G01N 27/4077; G01N 27/4071; G01N 27/419; G01N 33/0073; G01N 15/0656; G01M 15/102; Y02T 10/47; F01N 11/00; F02D 41/1454; F02D 41/1495
USPC .................. 73/23.31, 31.05, 114.69, 114.71, 73/114.72, 114.73; 204/424, 426, 428
See application file for complete search history.

(56) References Cited

U.S. PATENT DOCUMENTS

| 7,708,869 B2* | 5/2010 | Yamada ........................ 204/428 |
| 7,758,736 B2* | 7/2010 | Okumura et al. ............. 204/428 |
| 7,901,556 B2* | 3/2011 | Yamada ........................ 204/428 |
| 2010/0024524 A1 | 2/2010 | Ebner et al. |

FOREIGN PATENT DOCUMENTS

| JP | 2008-96419 A | 4/2008 |
| JP | 2010-523989 A | 7/2010 |

* cited by examiner

*Primary Examiner* — Peter Macchiarolo
*Assistant Examiner* — Mohammed Keramet-Amircola
(74) *Attorney, Agent, or Firm* — Sughrue Mion, PLLC (57) ABSTRACT

A protector (100) of a gas sensor (1) includes an inner protector (120) and an outer protector (110). The inner protector accommodates a gas sensor element (10) and has a tubular side wall (122) having inner gas introduction holes (130), and a bottom wall (124). The outer protector has a tubular side wall (112) having outer gas introduction holes (115), a frustum-like taper wall (117) tapering frontward and an outer gas discharge hole (170) formed inside a front end edge (117s) of the taper wall. When SL represents an area defined by the front end edge of the taper wall, the area S of the opening of the outer gas discharge hole satisfies the relational expression ½×SL≤S≤SL. A cover portion (127) and a bottom wall (124) are partially away from each other along the axial direction, thereby forming side openings (162).

10 Claims, 8 Drawing Sheets

GAS SENSOR

TECHNICAL FIELD

The present invention relates to a gas sensor having a protector for protecting a gas sensor element exposed to a gas-to-be-measured from adhesion of water.

BACKGROUND ART

A conventionally known gas sensor has a gas sensor element for measuring the concentration of a particular gas, such as $NO_x$ (nitrogen oxides) or oxygen, contained in exhaust gas from an automobile or the like on the basis of electromotive force which is generated according to the differential of concentration of the particular gas and whose magnitude varies with the differential of concentration. The gas sensor is mounted, for use, to an automotive exhaust pipe or the like. Since the gas sensor element becomes high in temperature through exposure to high-temperature exhaust gas and through application of heat from a heater or the like, for example, when water contained in exhaust gas, or condensed water adhering to the inner surface of the exhaust pipe adheres to the gas sensor element, the gas sensor element may crack or fracture from thermal shock.

Thus, there has been developed a technique for protecting the gas sensor element from adhesion of water by means of covering the gas sensor element with a protector (refer to, for example, Patent Document 1). This protector has a dual structure composed of an inner protector and an outer protector. A gas-to-be-measured is introduced into the protector through gas introduction holes formed in the inner and outer protectors. Also, gas discharge holes are formed in side walls of a recess portion of a front end wall of the inner protector, whereby a water droplet which comes flying from the ambient atmosphere (from the front side of the gas sensor element) is unlikely to come in direct contact with the gas sensor element. Also, according to this technique, a taper portion formed between a bottom wall and a side wall of the inner protector projects frontward from the outer protector.

PRIOR ART DOCUMENTS

Patent Documents

[Patent Document 1] Japanese Patent Application Laid-Open (kokai) No. 2008-96419
[Patent Document 2] PCT Application Laid-Open No. 2010-523989

SUMMARY OF THE INVENTION

Problems to be Solved by the Invention

However, in the case of the gas sensor of Patent Document 1, since the bottom wall provided at the front end of the taper portion is formed relatively large as compared with the taper portion, the generation of a negative pressure in the vicinity of the taper portion is less intensive. Thus, difficulty is encountered in discharging exhaust gas introduced into the interior space of the inner protector to the ambient atmosphere through the gas discharge holes. Therefore, the responsiveness of the gas sensor may deteriorate.

In this connection, there has been developed a gas sensor having a protection cap which has a tubular sensor element chamber covering a sensor element, and an anterior chamber surrounding the exterior of the sensor element chamber, as well as having a wedge-like nozzle (a device for accelerating a flow) at the front end of the sensor element chamber (refer to, for example, Patent Document 2). In this gas sensor, the nozzle has an outlet hole opening at its front end and accelerates a flow in the sensor element chamber, thereby discharging particles and condensed liquid from inside the sensor element chamber through the outlet hole.

However, in the case of the gas sensor of Patent Document 2, since the outlet hole opening at its front end directly faces the sensor element, there is a problem that a water droplet which comes flying from the ambient atmosphere (from the front side of the gas sensor element) is apt to come into contact with the sensor element through the outlet hole.

The present invention has been conceived to solve the above problem, and an object of the invention is to provide a gas sensor having a protector which exhibits greatly improved gas discharge performance to thereby enhance responsiveness of the gas sensor and which can effectively protect a gas sensor element from adhesion of water.

Means for Solving the Problems

To achieve the above object, a gas sensor of the present invention comprises a gas sensor element extending in a direction of an axis and having a detection portion at its front end portion for detecting a gas-to-be-measured; a tubular metallic shell holding the gas sensor element in such a manner as to allow the detection portion to project from its front end; and a protector fixed to a front end portion of the metallic shell and enclosing the detection portion. The protector comprises an inner protector and an outer protector. The inner protector accommodates the detection portion of the gas sensor element in its interior space and has a tubular side wall having an inner gas introduction hole for introducing the gas-to-be-measured into the interior space, and a bottom wall provided at a front end of the side wall. The outer protector accommodates the inner protector therein with a gap formed between the outer protector and the side wall of the inner protector and has a tubular side wall having an outer gas introduction hole provided frontward of the inner gas introduction hole with respect to the direction of the axis and adapted to introduce the gas-to-be-measured into the gap. The outer protector has a frustum-like taper wall tapering frontward from a front end of the side wall with respect to the direction of the axis and an outer gas discharge hole formed inside a front end edge of the taper wall and establishing communication between the interior and the exterior of the outer protector. When SL represents an area defined by the front end edge of the taper wall, the outer gas discharge hole has an area S which satisfies a relational expression $\frac{1}{2} \times SL \leq S \leq SL$. The bottom wall of the inner protector has a bottom wall opening; the inner protector has a cover portion covering the bottom wall opening from a rear side with respect to the direction of the axis and recessed rearward of the bottom wall with respect to the direction of the axis; and the cover portion and the bottom wall are formed partially away from each other along the direction of the axis, thereby forming a side opening.

According to the thus-configured gas sensor, the outer protector has the frustum-like taper wall tapering frontward from the front end of the side wall with respect to the direction of the axis, and the outer gas discharge hole opens in the frustum base at the front end of the outer protector in such a manner as to satisfy the relational expression $\frac{1}{2} \times SL \leq S \leq SL$. Thus, a strong negative pressure is generated in the vicinity of the front end of the taper wall on the downstream side with respect to a flow of the gas-to-be-measured, thereby intensifying the effect of sucking out the gas-to-be-measured which has been introduced into the interior space of the inner protector, from the outer gas discharge hole via the bottom wall opening of the inner protector. Therefore, responsiveness of the gas sensor can be improved. In the case of the relational expression S<½×SL, a bottom wall formed at the frustum base of the front end of the outer protector becomes relatively large as compared with the taper wall, potentially resulting in a failure to yield the above effect.

Meanwhile, when the outer gas discharge hole is formed in the frustum base at the front end of the outer protector, difficulty is encountered in providing a recess portion as described in Patent Document 1.

Thus, according to the gas sensor of the present invention, the bottom wall opening is formed in the bottom wall of the inner protector in such a manner as to be covered with the cover portion from the rear side with respect to the direction of the axis. By virtue of this configurational feature, even when a water droplet or the like comes flying along the direction of the axis into the bottom wall opening through the outer gas discharge hole, the cover portion blocks off the water droplet or the like. Therefore, the water droplet or the like is unlikely to directly reach the gas sensor element, whereby the gas sensor element can be protected from adhesion of water.

Furthermore, the gas sensor of the present invention may be configured such that, as viewed in the direction of the axis, the bottom wall opening and the outer gas discharge hole overlap each other.

In the thus-configured gas sensor, since the bottom wall opening (the cover portion) and the outer gas discharge hole at least partially overlap each other, by means of the bottom wall opening and the outer gas discharge hole being located in close proximity to each other, the gas-to-be-measured can flow from the inner protector to the ambient atmosphere along the direction of the axis. Therefore, responsiveness of the gas sensor can be further improved.

Furthermore, the gas sensor of the present invention may be configured such that, as viewed in the direction of the axis, the side opening and the outer gas discharge hole overlap each other.

In the thus-configured gas sensor, since the side opening of the inner protector and the outer gas discharge hole at least partially overlap each other, the side opening and the outer gas discharge hole can be located in proximity to each other. Thus, as compared with the configuration in which the bottom wall opening and the outer gas discharge hole merely overlap each other, the gas-to-be-measured can flow to a greater extent from the inner protector to the ambient atmosphere along the direction of the axis. Therefore, responsiveness of the gas sensor can be further improved.

Furthermore, the gas sensor of the present invention may be configured such that the side wall of the inner protector has a drain hole, and the drain hole does not overlap in position along the direction of the axis with the outer gas introduction hole and overlaps in position along the direction of the axis with the side opening.

According to the thus-configured gas sensor, by virtue of provision of the drain hole in the side wall of the inner protector, even when a water droplet enters through the outer gas introduction hole of the outer protector, the water droplet can be introduced into the inner protector through the drain hole, thereby preventing entry of the water droplet through the inner gas introduction hole. Additionally, since the drain hole and the side opening are located in proximity to each other, the water droplet which has entered the inner protector through the drain hole is immediately drained out (toward the outer gas discharge hole) through the side opening with ease.

Meanwhile, since the drain hole does not overlap with the outer gas introduction hole, a gaseous component which has passed through the outer gas introduction hole can be restrained from directly passing through the drain hole, thereby maintaining the amount of the gas-to-be-measured to be introduced into the inner protector through the inner gas introduction hole and, in turn, maintaining responsiveness of the gas sensor.

Furthermore, the gas sensor of the present invention may be configured such that a minimum width of the outer gas discharge hole is greater than a maximum length of the side opening along the direction of the axis.

According to the thus-configured gas sensor, the gas-to-be-measured which has flowed out from the inner protector through the side opening can be discharged to the ambient atmosphere without involvement of stagnation within the outer protector, which could otherwise result from throttling by the outer gas discharge hole. Thus, deterioration in responsiveness of the gas sensor can be restrained.

Furthermore, the gas sensor of the present invention may be configured such that the minimum width of the outer gas discharge hole is 2 mm or greater. By virtue of this configurational feature, a water droplet which has passed through the side opening can be readily drained out through the outer gas discharge hole without involvement of stagnation within the outer protector. When the minimum width of the outer gas discharge hole is less than 2 mm, this effect may fail to be yielded.

Furthermore, the gas sensor of the present invention may be configured such that the maximum length of the side opening along the direction of the axis is 1.6 mm or greater. This configurational feature enhances the effect of discharging the gas-to-be-measured which has been introduced into the interior space, to the exterior of the inner protector (within the outer protector), whereby responsiveness of the gas sensor can be improved. When the maximum axial length of the side opening is less than 1.6 mm, this effect may fail to be yielded.

Furthermore, the gas sensor of the present invention may be configured such that the side wall of the inner protector has a stepped portion which has a front-oriented surface and expands radially outward along a rearward direction and such that the stepped portion is located within a range along the direction of the axis between the outer gas introduction hole and the inner gas introduction hole.

According to the thus-configured gas sensor, when the gas-to-be-measured which contains water is introduced through the outer gas introduction hole, a gaseous component, whose specific gravity is small, ascends and is introduced into the inner protector through the inner gas introduction hole, whereas water collides against the stepped portion (the front-oriented surface) of the inner protector and drops. Thus, entry of water into the inner protector can be avoided.

Effect of the Invention

The present invention can greatly improve gas discharge performance to thereby enhance responsiveness of a gas sensor and can effectively protect a gas sensor element from adhesion of water.

MODES FOR CARRYING OUT THE INVENTION

Figure 1:
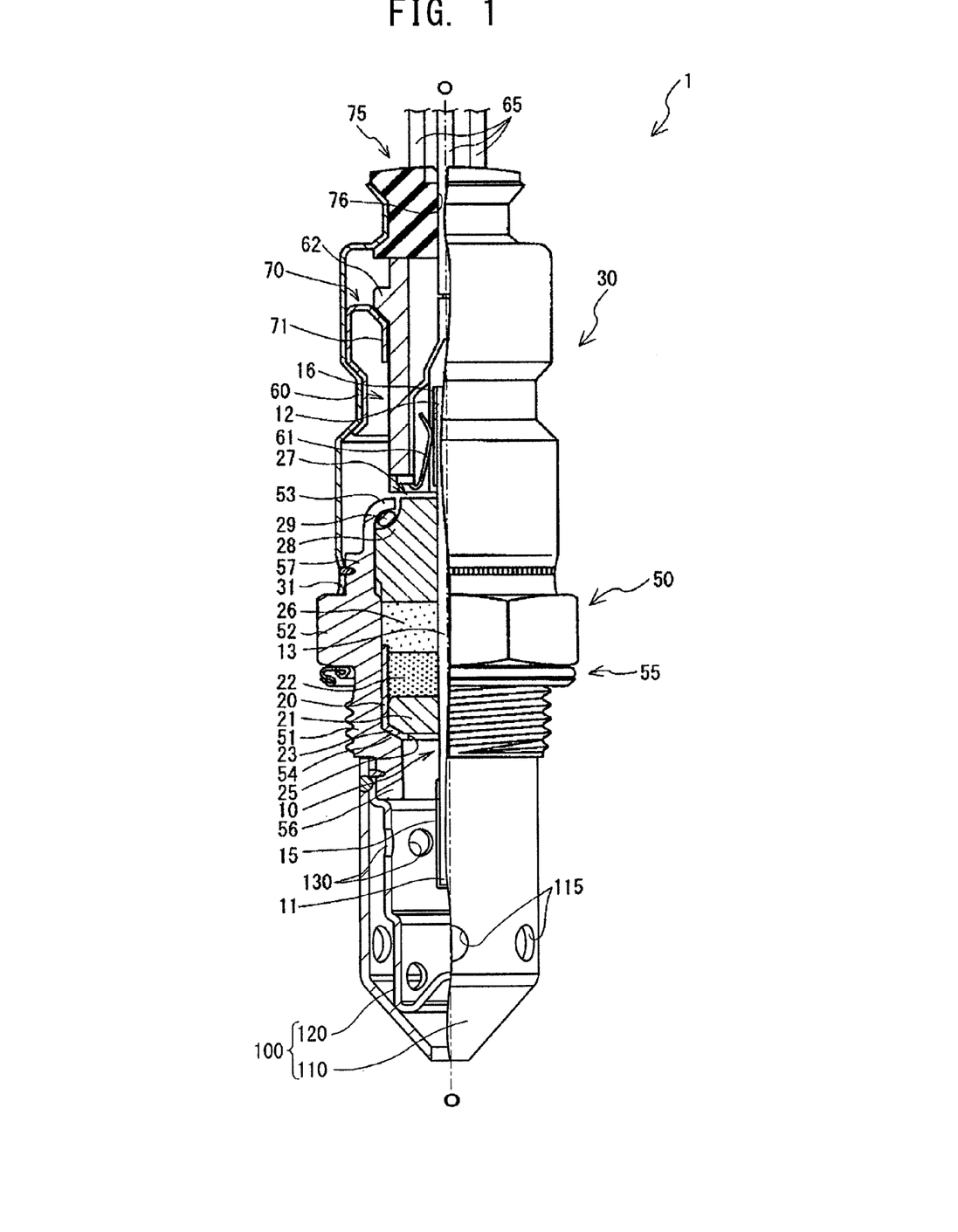
FIG. 1 Partially sectional view, taken along the direction of the axis, of a gas sensor according to a first embodiment of the present invention.

Embodiments of the present invention will next be described with reference to the drawings. FIG. 1 is a partially sectional view, taken along the direction of an axis O, of a gas sensor 1 according to a first embodiment of the present invention. The gas sensor 1 is a so-called full range air/fuel ratio sensor which holds therein a gas sensor element 10 and is mounted to an automotive exhaust pipe (not shown). A detection portion 11 of the gas sensor element 10 is exposed to exhaust gas which flows through the exhaust pipe, thereby detecting the air/fuel ratio of the exhaust gas from oxygen concentration in the exhaust gas.

In the following description, the direction of the axis O of the gas sensor 1 is referred to as the vertical direction, and a side toward the detection portion 11 of the gas sensor element 10 of the gas sensor 1 is referred to as the front side of the gas sensor 1, and a side toward a rear end portion 12 of the gas sensor element 10 as the rear side (proximal side) of the gas sensor 1.

The gas sensor element 10 has a narrow plate-like shape extending in the direction of the axis O as known publicly. The gas sensor element 10 assumes the form of a substantially rectangular columnar laminate in which a gas detecting body for detecting oxygen concentration and a heater body for quickly activating the gas detecting body through application of heat are affixed to each other (the left-right direction of the paper on which FIG. 1 appears is the plate thickness direction, and the front-back direction of the paper is the plate width direction). The gas detecting body is composed of a solid electrolyte body which predominantly contains zirconia, and electrodes which predominantly contains platinum (these members are not shown). The electrodes are disposed at the detection portion 11 located at a front end portion of the gas sensor element 10. In order to protect the electrodes from poisoning by exhaust gas, the detection portion 11 of the gas sensor element 10 is covered with a protection layer 15. The rear end portion 12 of the gas sensor element 10 has five electrode pads 16 (one of which is shown in FIG. 1) for allowing external connection with electrodes extending from the gas detecting body and the heater body. The present embodiment is described while mentioning the gas sensor element 10 as the equivalent of the "gas sensor element" in the present invention. However, in a strict sense, the heater body is not necessarily required as a constituent of the gas sensor element; thus, the gas detecting body corresponds to the "gas sensor element" in the present invention.

A closed-bottomed tubular metal cup 20 is disposed at a position corresponding to a frontward subportion of a central trunk portion 13 of the gas sensor element 10 in such a manner that the gas sensor element 10 is inserted through the interior of the metal cup 20 with the detection portion 11 projecting from an opening 25 formed in the bottom of the metal cup 20. The metal cup 20 is a member for holding the gas sensor element 10 in a metallic shell 50. A front-end peripheral portion 23 located at a peripheral portion of the bottom of the metal cup 20 is tapered toward a tubular wall portion of the metal cup 20. The metal cup 20 contains a ceramic ring 21 made of alumina and a talc ring 22 formed by compacting a talc powder, in such a manner that the gas sensor element 10 is inserted through the ceramic ring 21 and through the talc ring 22. The talc ring 22 is crushed within the metal cup 20 so as to tightly fill an associated space, thereby holding the gas sensor element 10 in position in the metal cup 20.

An assembly of the metal cup 20 and the gas sensor element 10 is surrounded by and held by the tubular metallic shell 50. The metallic shell 50 is adapted to fixedly attach the gas sensor 1 to an automotive exhaust pipe (not shown). The metallic shell 50 is formed from a low-carbon steel such as SUS430 and has an externally threaded portion 51 which is formed on an outer circumferential surface of the metallic shell 50 and located on a side toward the front end of the metallic shell 50. The metallic shell 50 has a front-end engagement portion 56 which is located frontward of the externally threaded portion 51 and engaged with a protector 100, which will be described later. The metallic shell 50 also has a tool engagement portion 52 which is formed at an axially central portion of the outer circumferential surface of the metallic shell 50 and with which a mounting tool is engaged. In order to prevent leakage of gas when the gas sensor 1 is attached to the exhaust pipe, a gasket 55 is fitted to a portion of the metallic shell 50 between the front end face of the tool engagement portion 52 and the rear end of the externally threaded portion 51. The metallic shell 50 further has a rear-end engagement portion 57 which is located rearward of the tool engagement portion 52 and with which a tubular sheath 30 to be described later is engaged, and a crimp portion 53 which is located rearward of the rear-end engagement portion 57 and adapted to crimp-hold the gas sensor element 10 in the metallic shell 50.

The metallic shell 50 has a stepped portion 54 on its inner circumferential surface at a position substantially corresponding to the externally threaded portion 51. The front-end peripheral portion 23 of the metal cup 20 which holds the gas sensor element 10 is engaged with the stepped portion 54. Furthermore, a talc ring 26 is placed into the metallic shell 50 along the inner circumference of the metallic shell 50 toward the rear end of the metal cup 20 in such a state that the gas sensor element 10 is inserted through the talc ring 26. A tubular sleeve 27 is fitted into the metallic shell 50 in such a manner as to press the talc ring 26 from the rear end of the talc ring 26. The sleeve 27 has a step-like shoulder portion 28 formed on the outer circumferential surface of a rear end portion of the sleeve 27. An annular crimp packing 29 is disposed on the shoulder portion 28. In this condition, the crimp portion 53 of the metallic shell 50 is crimped in such a manner as to press the shoulder portion 28 of the sleeve 27 frontward via the crimp packing 29. Being pressed by the sleeve 27, the talc ring 26 is crushed within the metallic shell 50, thereby tightly filling an associated space. By means of the talc ring 26 and the talc ring 22, which is previously placed in the metal cup 20, the metal cup 20 and the gas sensor element 10 are held in position in the metallic shell 50.

The rear end portion 12 of the gas sensor element 10 projects rearward beyond the rear end (crimp portion 53) of the metallic shell 50. The rear end portion 12 is covered with a tubular separator 60 formed from an electrically insulative ceramic. The separator 60 internally holds five connection terminals 61 (one of which is shown in FIG. 1) electrically connected to the five electrode pads 16 formed on the rear end portion 12 of the gas sensor element 10. Also, the separator 60 protectively accommodates connections between the connection terminals 61 and corresponding five lead wires 65 (three of which are shown in FIG. 1), which extend to the exterior of the gas sensor 1.

The tubular sheath 30 is disposed in such a manner as to surround the rear end portion 12 of the gas sensor element 10 to which the separator 60 is fitted. The tubular sheath 30 is made of stainless steel (e.g., SUS304). A front open end 31 of the tubular sheath 30 is engaged with the outer circumference of the rear-end engagement portion 57 of the metallic shell 50. The open end 31 is crimped radially inward, and laser welding is performed on the open end 31 along the entire outer circumference of the open end 31, whereby the open end 31 is joined to the rear-end engagement portion 57. The tubular sheath 30 and the metallic shell 50 are thus fixedly united together.

A tubular metal holder 70 is disposed in the gap between the tubular sheath 30 and the separator 60. The metal holder 70 has a support portion 71, which is formed by inwardly bending a rear end of the metal holder 70. The separator 60 is inserted through the metal holder 70 such that a flange portion 62 formed on the outer circumference of a rear end portion of the separator 60 is engaged with the support portion 71, whereby the separator 60 is supported by the support portion 71. In this condition, a portion of the tubular sheath 30 where the metal holder 70 is disposed is crimped radially inward, whereby the metal holder 70 which supports the separator 60 is fixed to the tubular sheath 30.

A grommet 75 made of fluorine-containing rubber is fitted into a rear end opening of the tubular sheath 30. The grommet 75 has five insertion holes 76 (one of which is shown in FIG. 1). The five lead wires 65 extending outwardly from the separator 60 are airtightly inserted through the respective insertion holes 76. In this condition, while the grommet 75 presses the separator 60 frontward, a portion of the tubular sheath 30 which corresponds to the grommet 75 is crimped radially inward, whereby the grommet 75 is fixed to the rear end of the tubular sheath 30.

Meanwhile, the detection portion 11 of the gas sensor element 10 held by the metallic shell 50 projects from a front end portion (the front-end engagement portion 56) of the metallic shell 50. The protector 100 is fitted to the front-end engagement portion 56 of the metallic shell 50 for protecting the detection portion 11 of the gas sensor element 10 from fouling with deposits (poisoning substances, such as fuel ash and oil) contained in exhaust gas and from breakage caused by adhesion of water contained in exhaust gas or condensed water adhering to the inner surface of the exhaust pipe. The protector 100 is fixed to the front-end engagement portion 56 by spot welding or laser welding. Hereinafter, this protector 100 will be described with reference to FIGS. 2 to 4.

Figure 2:
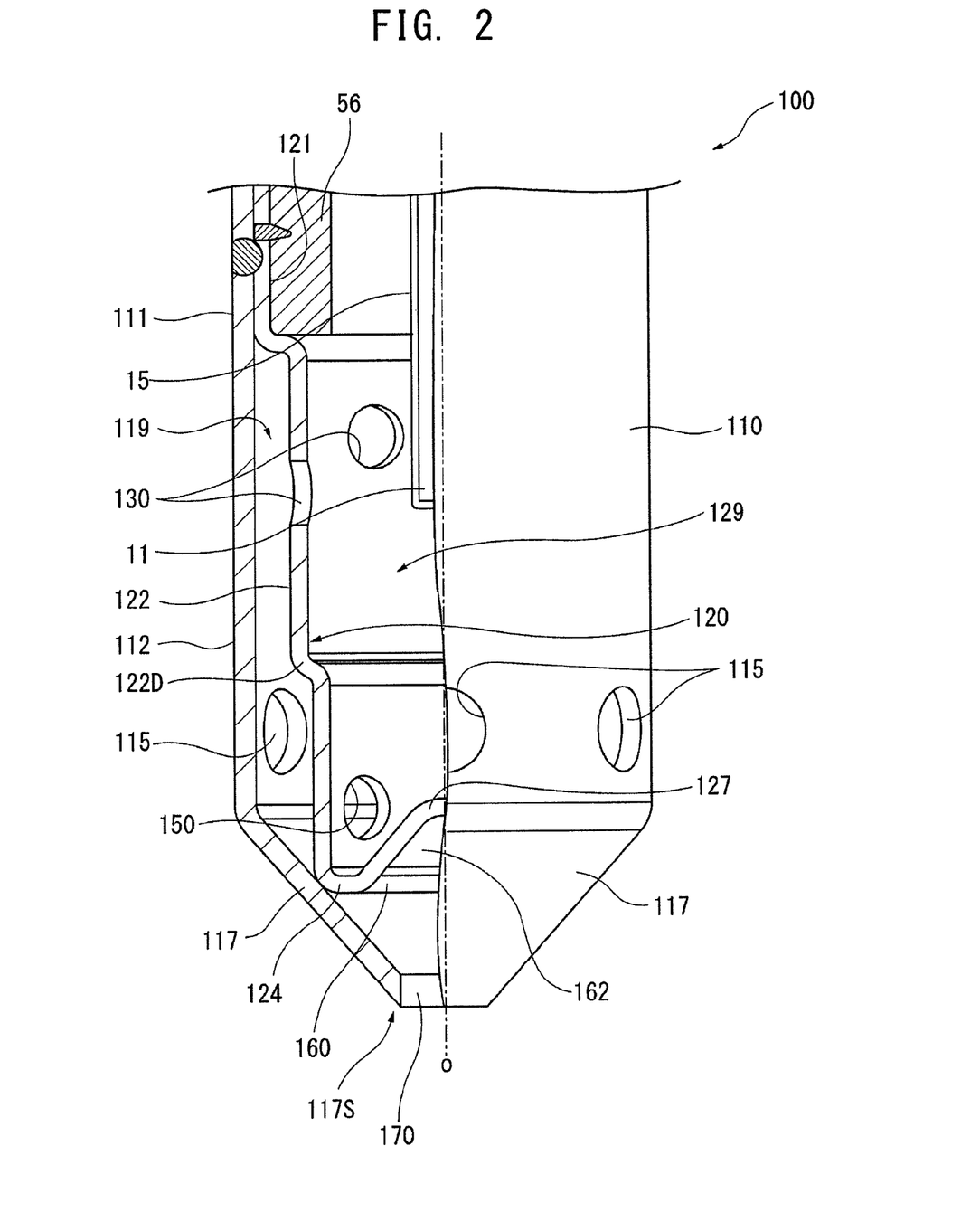
FIG. 2 Enlarged partially sectional view of a protector.

As shown in FIG. 2, the protector 100 has a dual structure composed of a closed-bottomed tubular inner protector 120 and an outer protector 110. The inner protector 120 has a bottom wall 124 and a side wall 122. The outer protector 110 has a tubular side wall 112 which radially surrounds the inner protector 120 with a gap (hereinafter, may be referred to as the "gas separation chamber" 119) formed relative to the outer circumferential surface of the inner protector 120.

The inner protector 120 is smaller in outside diameter than the front-end engagement portion 56 of the metallic shell 50 and has an open end portion 121 which is an end portion on a side toward opening (on a side toward a proximal end) and which is expanded in diameter so as to be engaged with the outer circumference of the front-end engagement portion 56. Laser welding is performed on the open end portion 121 along the entire outer circumference of the open end portion 121, whereby the inner protector 120 is fixed to the front-end engagement portion 56 of the metallic shell 50. Meanwhile, the side wall 122 of the inner protector 120 has a plurality of (six in the present embodiment) inner gas introduction holes 130 formed therein along the circumferential direction and located toward the open end portion 121 with respect to the direction of the axis O. The inner gas introduction holes 130 are provided for introducing mainly a gaseous component of exhaust gas introduced into the gas separation chamber 119 through outer gas introduction holes 115 of the outer protector 110, which will be described later, into the interior of the inner protector 120; i.e., into a gas detection chamber (which corresponds to the "interior space" appearing in a claim) 129 to which the detection portion 11 of the gas sensor element 10 is exposed.

Also, the side wall 122 of the inner protector 120 has a plurality of (four in the present embodiment) drain holes 150 formed therein along the circumferential direction and located toward the front end of the side wall 122. The drain holes 150 are provided for discharging water (water droplets) and the like contained in exhaust gas introduced into the gas separation chamber 119, to the exterior of the inner protector 120 via the gas detection chamber 129. The drain holes 150 are disposed frontward of the inner gas introduction holes 130.

Figure 3:
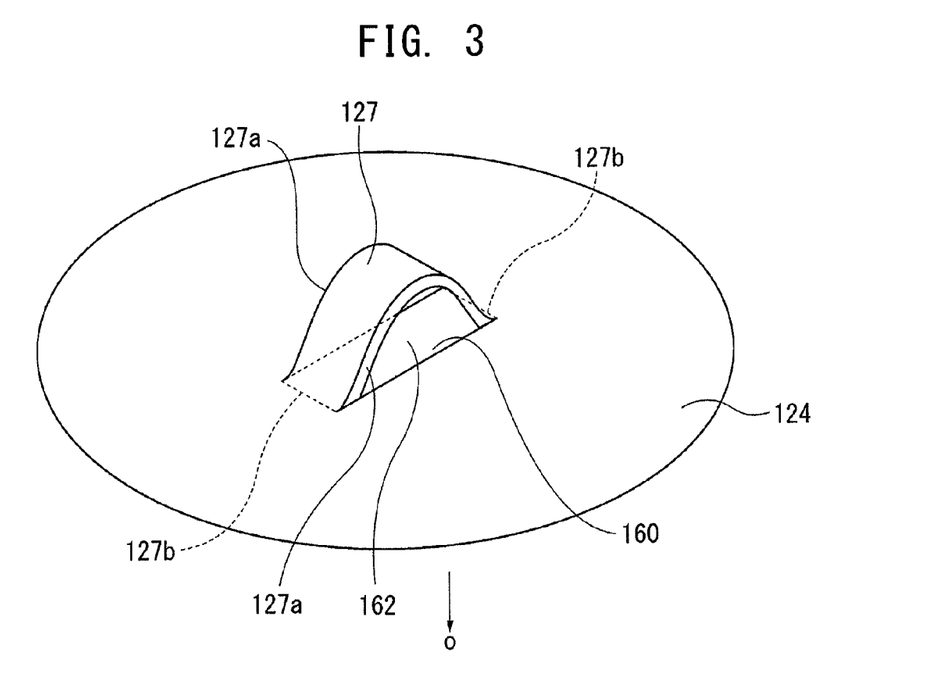
FIG. 3 Perspective view showing a cover portion and a bottom wall opening formed in a bottom wall of an inner protector.

The bottom wall 124 of the inner protector 120 is substantially parallel to a plane perpendicular to the direction of the axis O. A portion (a central portion) of the bottom wall 124 is recessed rearward in such a manner as to be pressed axially inward, thereby forming a cover portion 127. Specifically, as shown in FIG. 3, two parallel slits 127a are formed in a central portion of the bottom wall 124. A strip-like portion of the bottom wall 124 between the slits 127a is pressed rearward, thereby forming the cover portion 127 in a protruding manner. The cover portion 127 and the bottom wall 124 are away from each other along the direction of the axis O at the slits 127a, whereas the cover portion 127 and the bottom wall 124 are connected together at short sides 127b (line segments which connect ends of the opposed slits 127a).

In this manner, the cover portion 127 is supported by the bottom wall 124 in such a condition that a subportion of the cover portion 127 is separated from the bottom wall 124 along the direction of the axis O (in such a condition that "the cover portion and the bottom wall are partially away from each other along the direction of the axis" as mentioned in a claim). A bottom wall opening 160 opens in a portion of the bottom wall 124 which, as viewed in the direction of the axis O, coincides with the cover portion 127. Furthermore, side openings 162 are formed at an angle with the direction of the axis O in respective regions (associated with the slits 127a) where the cover portion 127 and the bottom wall 124 are away from each other along the direction of the axis O, and communicate with the bottom wall opening 160. The bottom wall opening 160 allows exhaust gas and water droplets which have been introduced into the gas detection chamber 129, to be discharged to the exterior of the inner protector 120 through the side openings 162.

When the maximum length of the side openings 162 along the direction of the axis O is 1.6 mm or greater, the effect of discharging exhaust gas which has been introduced into the gas detection chamber 129, to the exterior of the inner protector 120 (into the outer protector 110) is intensified, whereby responsiveness of the gas sensor 1 can be improved.

This is based on the results of the following responsiveness evaluation test.

Specifically, responsiveness was evaluated by the following method. The theoretical air/fuel ratio (air/gasoline ratio) 14.7 was represented by a λ value of 1, and the rich condition (λ=0.97) and the lean condition (λ=1.03) were forcibly changed over to each other. Time until the output value of the gas sensor 1 changed to a value corresponding to λ=1 after changeover from the rich condition to the lean condition was measured. In this evaluation, the gas sensor 1 was mounted to the exhaust pipe of a 4-cycle engine of 2,000 cc displacement, and the engine was driven at a speed of 2,000 rpm. The gas sensor 1 was mounted to the exhaust pipe at a position where the temperature of engine exhaust was about 450° C.

Evaluation samples were the gas sensors 1 having a maximum length of the side openings 162 along the direction of the axis O of 0.9 mm, 1.2 mm, and 1.6 mm. The samples were evaluated by the above-mentioned evaluation method.

The samples exhibited a time of 620 sec (length along the direction of the axis O: 0.9 mm), a time of 585 sec (length along the direction of the axis O: 1.2 mm), and a time of 560 sec (length along the direction of the axis O: 1.6 mm), respectively. If the time is 560 sec, the gas sensor 1 exhibits sufficient responsiveness in actual use.

Meanwhile, the outer protector 110 is greater in outside diameter than the front-end engagement portion 56 of the metallic shell 50 and has an open end portion 111 which is an end portion on a side toward opening (on a side toward a proximal end) and which is engaged with the outer circumference of the front-end engagement portion 56 (more specifically, with the outer circumference of the open end portion 121 of the inner protector 120). Laser welding is performed on the open end portion 111 along the entire outer circumference of the open end portion 111, whereby the outer protector 110 is fixed to the front-end engagement portion 56 of the metallic shell 50. Meanwhile, the side wall 112 of the outer protector 110 has a plurality of (six in the present embodiment) outer gas introduction holes 130 formed therein along the circumferential direction and located toward the front end with respect to the direction of the axis O. The outer gas introduction holes 110 are provided for introducing exhaust gas into the gas separation chamber 119 from the ambient atmosphere. The outer gas introduction holes 115 are disposed frontward of the inner gas introduction holes 130 with respect to the direction of the axis O.

The outer protector 110 has a frustum-like (frustum-of-cone-like in the present embodiment) taper wall 117 tapering frontward from the front end of the side wall 112 with respect to the direction of the axis O. Also, the outer protector 110 has an outer gas discharge hole 170 formed inside a front end edge 117s of the taper wall 117 and establishing communication between the interior and the exterior of the outer protector 110.

Figure 4A:
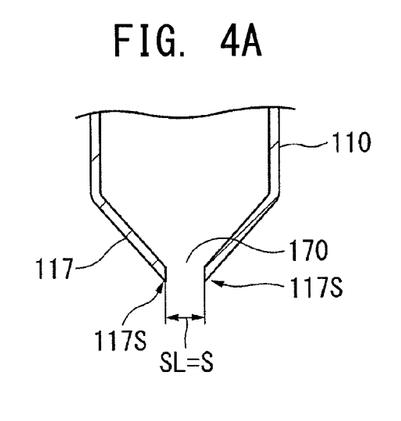
FIGS. 4A and 4B Enlarged, fragmentary, sectional views showing the front end edge of a taper wall and its periphery.
Figure 4B:
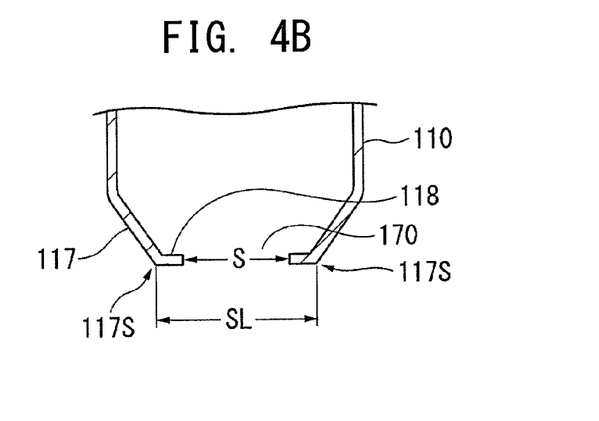

As shown in FIG. 4A, in the first embodiment, the front end edge 117s of the taper wall 117 and the perimeter of the outer gas discharge hole 170 coincide with each other; i.e., the outer gas discharge hole 170 is formed by cutting off the entire frustum base (an imaginary plane surrounded by the front end edge 117s) of the taper wall 117, thereby extending through the entire frustum base in the direction of the axis O. Therefore, when SL represents an area defined by the front end edge 117s of the taper wall 117, the area S of the outer gas discharge hole 170 is equal to SL. However, in the present invention, it suffices that the area S satisfies the relational expression $\frac{1}{2} \times SL \leq S \leq SL$. For example, as shown in FIG. 4B, the following configuration may be employed: the outer gas discharge hole 170 is located radially inward of the front end edge 117s of the taper wall 117, and an outer bottom wall 118 is formed in such a manner as to extend from the front end edge 117s to the perimeter of the outer gas discharge hole 170.

Preferably, the minimum width of the outer gas discharge hole 170 is 2 mm or greater (in the case where the outer gas discharge hole 170 is circular, the area of the outer gas discharge hole 170 is 3.14 mm² or greater) for the following reason: water droplets which have passed through the side openings 162 are likely to pass through the outer gas discharge hole 170 by their own weight without involvement of stagnation within the outer gas protector 110 to thereby be discharged to the ambient atmosphere.

This is based on the results of the following evaluation test.

Specifically, evaluation samples were assemblies each configured such that the outer protector 110 was fixed to the metallic shell 50. The outer protectors 110 of the samples had a minimum width of the outer gas discharge hole 170 of 0.1 mm, 0.15 mm, and 0.2 mm, respectively.

The samples were evaluated by the following method. Water was dropped into the outer protector 110 from a side toward the metallic shell 50 to check to see if water is discharged through the outer gas discharge hole 170 of the outer protector 110. Also, the amount of water which had been dropped until water was discharged through the outer gas discharge hole 170 of the outer protector 110 was measured.

The amounts of dropped water were 600 μl (minimum width: 0.1 mm), 600 μl (minimum width: 0.15 mm), and 280 μl (minimum width: 0.2 mm). Thus, it is known that when the minimum width of the outer gas discharge hole 170 of the outer protector 110 is 0.2 mm or greater, water droplets are likely to be discharged to the ambient atmosphere through the outer gas discharge hole 170.

Preferably, the taper angle of the taper wall 117 is 30° to 60° for the following reason. Through employment of such a taper angle, even when an angle at which the gas sensor 1 is mounted to an object body (exhaust pipe or the like) changes, the taper wall 117 has an angle with a gas flow within the object body; thus, a backward gas flow into the outer protector 110 through the outer gas discharge hole 170 is unlikely to occur.

Furthermore, when the minimum width of the outer gas discharge hole 170 is rendered greater than the length of the side openings 162 along the direction of the axis O, exhaust gas which has passed through the side openings 162 from the gas detection chamber 12 can be discharged to the ambient atmosphere without involvement of stagnation within the outer protector 110, which could otherwise result from throttling by the outer gas discharge hole 170. Thus, deterioration in responsiveness of the gas sensor 1 can be restrained.

In this manner, the outer protector 110 has the frustum-like taper wall 117 tapering frontward from the front end of the side wall 112 with respect to the direction of the axis O and the outer gas discharge hole 170 which opens in the frustum base of the taper wall 117 in such a manner as to satisfy the relational expression ½×SL≤S≤SL. Thus, as will be described later, a strong negative pressure is generated in the vicinity of the front end of the taper wall 117 on the downstream side with respect to a flow of the gas-to-be-measured. The negative pressure effectively acts on the gas detection chamber 129, thereby intensifying the effect of sucking out exhaust gas which has been introduced into the gas detection chamber 129.

Furthermore, since the effect of sucking out exhaust gas through the outer gas discharge hole 170 is intensified, even when an angle at which the gas sensor 1 is mounted to an object body (exhaust pipe or the like) changes, a backward gas flow into the outer protector 110 through the outer gas discharge hole 170 is unlikely to occur. Thus, the gas-to-be-measured can be stably detected without involvement of variation in responsiveness. Particularly, for example, in the case where the gas sensor 1 is mounted at such a mounting angle that the front end of the gas sensor 1 is oriented upstream with respect to a gas flow, while the rear end of the gas sensor 1 is oriented downstream, a backward flow of water and gas into the protector can be effectively restrained.

Meanwhile, in the case of the relational expression ½×SL>S, the outer bottom wall 118 is formed relatively large as compared with the taper wall 117, thereby mitigating the shape effect associated with taper and thus shrinking a negative pressure region in the vicinity of the front end of the taper wall 117 on the downstream side with respect to a flow of the gas-to-be-measured.

Figure 5:
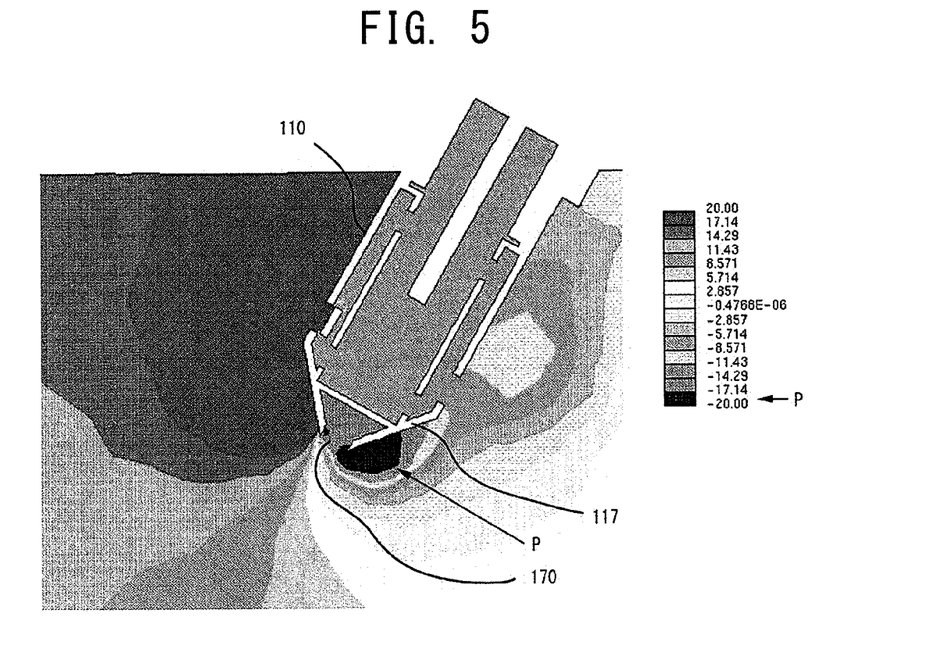
FIG. 5 View showing the results of numerical simulation of gas pressure distribution as observed when the gas sensor according to the first embodiment of the present invention is placed in a gas flow.
Figure 6:
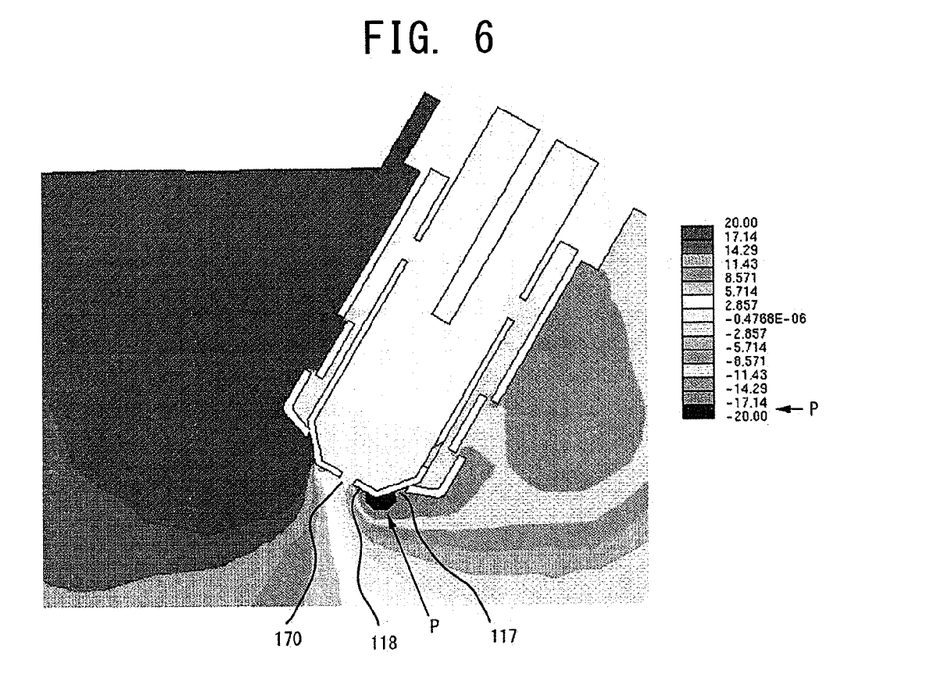
FIG. 6 View showing the results of numerical simulation of gas pressure distribution as observed when a gas sensor having a conventional protector is placed in a gas flow.

FIGS. 5 and 6 show the results of numerical simulation of gas pressure distributions as observed when the gas sensor 1 according to the first embodiment of the present invention and a gas sensor having the conventional protector (described in Patent Document 1) are placed in a gas flow. This numerical simulation is of turbulence analysis using the Navier-Stokes equation and was conducted by use of the fluid analysis software (product name: STAR-CD) supplied by CD-adapco JAPAN Co., LTD. (CAD). In FIGS. 5 and 6, a dark-colored region P is of a strong negative pressure (black color pointed by the arrow P in color tones of legends of FIGS. 5 and 6).

As is apparent from FIG. 5, in the case of the outer protector 110 having, at its front end, the frustum-like taper wall 117 tapering frontward with respect to the direction of the axis O and the outer gas discharge hole 170 which opens in the frustum base of the taper wall 117 in such a manner as to satisfy the relational expression ½×SL≤S≤SL (in FIG. 5, S=SL), a strong negative pressure is generated in the vicinity of the front end of the taper wall 117 on the downstream side with respect to a flow of gas (negative pressure region P).

By contrast, in the case of the conventional protector shown in FIG. 6, the outer bottom wall corresponding to the outer bottom wall 118 in FIG. 4B is formed relatively large as compared with the taper wall corresponding to the taper wall 117 in FIG. 4B (S=1/20SL). Thus, as is apparent from FIG. 6, there shrinks the negative pressure region P in the vicinity of the front end of the taper wall on the downstream side with respect to the gas flow.

Figure 7:
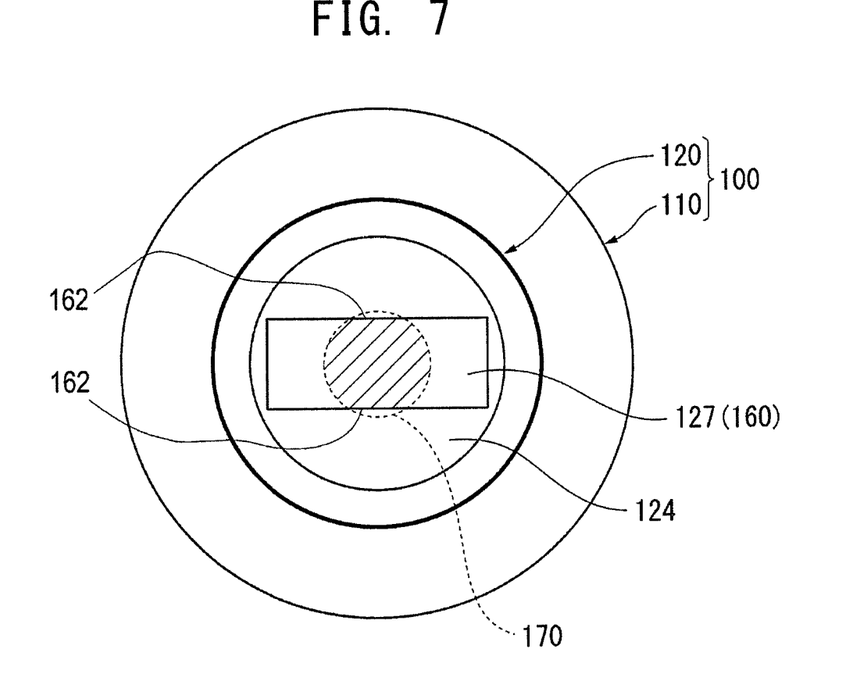
FIG. 7 Plan view showing a condition of overlapping of the bottom wall opening (cover portion) of the inner protector and an outer gas discharge hole of an outer protector as viewed frontward from the rear side of the gas sensor.

Furthermore, FIG. 7 shows a condition of overlapping of the bottom wall opening 160 (the cover portion 127) of the inner protector 120 and the outer gas discharge hole 170 of the outer protector 110 as viewed frontward from the rear side of the gas sensor 1.

As shown in FIG. 7, the bottom wall opening 160 (the cover portion 127) and the outer gas discharge hole 170 at least partially (hatched region in FIG. 7) overlap each other.

Furthermore, as shown in FIG. 7, the side openings 162 and the outer gas discharge hole 170 partially overlap each other.

In this manner, since the bottom wall opening 160 and the outer gas discharge hole 170 at least partially overlap each other, by means of the bottom, wall opening 160 and the outer gas discharge hole 170 being located in proximity to each other, the gas-to-be-measured can flow from the inner protector 120 to the ambient atmosphere along the direction of the axis O. Therefore, responsiveness of the gas sensor 1 can be further improved.

Furthermore, since the side openings 162 and the outer gas discharge hole 170 at least partially overlap each other, by means of the side openings 162 and the outer gas discharge hole 170 being located in proximity to each other, as compared with the configuration in which the bottom wall opening 160 and the outer gas discharge hole 170 merely overlap each other, the gas-to-be-measured can flow to a greater extent from the inner protector 120 to the ambient atmosphere along the direction of the axis O. Therefore, responsiveness of the gas sensor can be further improved.

As mentioned above, the gas sensor 1 according to the first embodiment is configured as follows: 1) the outer protector 110 has, at its front end, the frustum-like taper wall 117 tapering frontward with respect to the direction of the axis O and the outer gas discharge hole 170 which opens in the frustum base of the taper wall 117 in such a manner as to satisfy the relational expression ½×SL≤S≤SL, and 2) the bottom wall opening 160 is formed in the bottom wall 14 of the inner protector 120 in such a manner as to be covered with the cover portion 127 from the rear side.

By virtue of the configuration mentioned above in 1), a strong negative pressure is generated in the vicinity of the front end of the taper wall 117 on the downstream side with respect to a flow of the gas-to-be-measured, thereby intensifying the effect of sucking out exhaust gas which has been introduced into the gas detection chamber 129, from the outer gas discharge hole 170 via the bottom wall opening 160. Therefore, responsiveness of the gas sensor 1 can be improved.

Furthermore, according to the configuration mentioned above in 2), the bottom wall opening 160 is formed in the bottom wall 14 of the inner protector 120 accommodated in the outer protector 110, in such a manner as to be covered with the cover portion 127 from the rear side with respect to the direction of the axis O. By virtue of this configurational feature, even when a water droplet or the like comes flying along the direction of the axis O into the bottom wall opening 160 through the outer gas discharge hole 170, the cover portion 127 blocks off the water droplet or the like. Therefore, the water droplet or the like is unlikely to directly reach the gas sensor element 10, whereby the gas sensor element 10 can be protected from adhesion of water.

Figure 8:
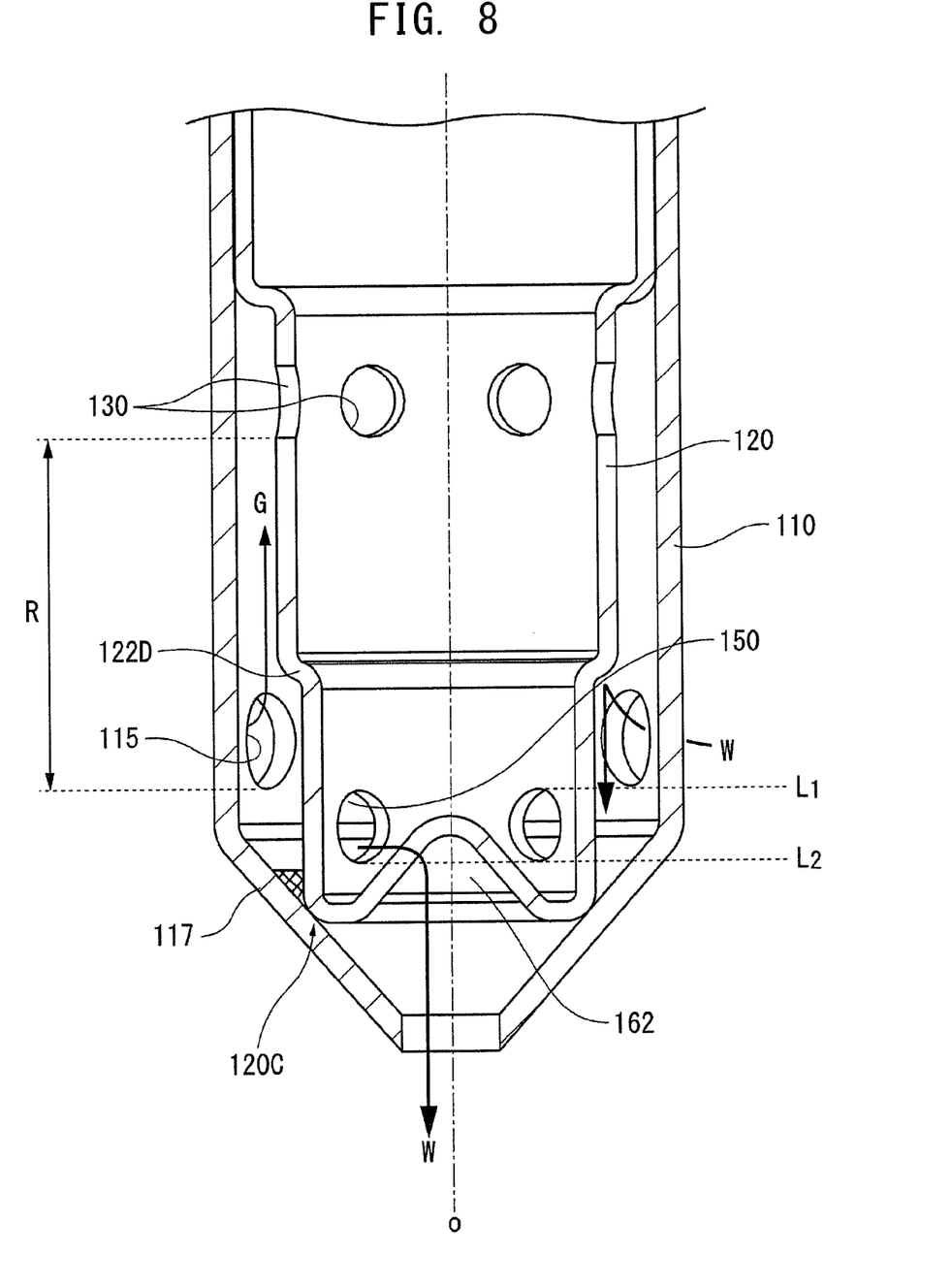
FIG. 8 Sectional view showing the positional relation along the direction of the axis among drain holes, inner gas introduction holes, outer gas introduction holes, side openings, and a stepped portion of a side wall of the inner protector.

Preferably, as shown in FIG. 8, the drain holes 150 of the inner protector 120 do not overlap in position along the direction of the axis O with the outer gas introduction holes 115, and the drain holes 150 overlap in position along the direction of the axis O with the side openings 162. The expression "the drain holes 150 of the inner protector 120 do not overlap in position along the direction of the axis O with the outer gas introduction holes 115" means that the front ends of the outer gas introduction holes 115 are located rearward of the rear ends $L_1$ of the drain holes 150. The expression "the drain holes 150 overlap in position along the direction of the axis O with the side openings 162" means that at least a portion of each of the side openings 162 is located between the positions of the rear ends L₁ and the front ends L₂ of the drain holes 150.

According to the above configuration, since the drain holes 150 and the side openings 162 are located in proximity to each other, water W which has entered the inner protector 120 through the drain holes 162 is immediately drained out (toward the outer gas discharge hole 170) through the side openings 162 with ease. Meanwhile, since the drain holes 150 do not overlap with the outer gas introduction holes 115, the gas-to-be-measured which has passed through the outer gas introduction holes 115 can be restrained from directly passing through the drain holes 150, thereby maintaining the amount of the gas-to-be-measured to be introduced into the gas detection chamber 129 of the inner protector 120 through the inner gas introduction holes 130 and, in turn, maintaining responsiveness of the gas sensor 1.

Also, preferably, as shown in FIG. 8, the side wall 122 of the inner protector 120 has a stepped portion 122D which has a front-oriented surface and expands radially outward along a rearward direction, and the stepped portion 122D is located within a range R along the direction of the axis O between the outer gas introduction holes 115 and the inner gas introduction holes 130. The range R extends between the front ends of the inner gas introduction holes 130 and the front ends of the outer gas introduction holes 115.

According to the above-mentioned configuration, when the gas-to-be-measured which contains water is introduced through the outer gas introduction holes 115, a gaseous component G, whose specific gravity is small, ascends and is introduced into the inner protector 120 through the inner gas introduction holes 130, whereas water W collides against the stepped portion 122D (the front-oriented surface) of the inner protector 120 and drops. Thus, entry of water into the gas detection chamber 129 of the inner protector 120 can be avoided.

In view of the above-mentioned draining effect, when a front end corner (a turnup between the side wall 122 and the bottom wall 124) 120c is in contact with the inner surface of the taper wall 117 of the outer protector 110, water (crosshatched portion in FIG. 8) collected between the inner protector 120 and the outer protector 110 encounters difficulty in draining (toward the outer gas discharge hole 170).

Therefore, in order to improve the draining effect, preferably, a gap is formed between the front end corner 120c and the inner surface of the taper wall 117.

Meanwhile, when a gap is formed between the front end corner 120c and the inner surface of the taper wall 117, the gas-to-be-measured which has been introduced through the outer gas introduction holes 115 passes through the gap. Thus, the gap is not preferred in terms of responsiveness of the gas sensor 1. Therefore, in view of responsiveness of the gas sensor 1, preferably, the front end corner 120c of the inner protector 120 is in contact with the inner surface of the taper wall 117 of the outer protector 110.

Next, a gas sensor 2 according to a second embodiment of the present invention will be described with reference to FIGS. 9 to 11. Since the gas sensor 2 according to the second embodiment is similar to the first embodiment except the configuration of cover portions 227 and bottom wall openings 260 provided in the bottom wall 124 of the inner protector 120, configurational features similar to those of the first embodiment are denoted by like reference numerals, and repeated description thereof is omitted.

Figure 9:
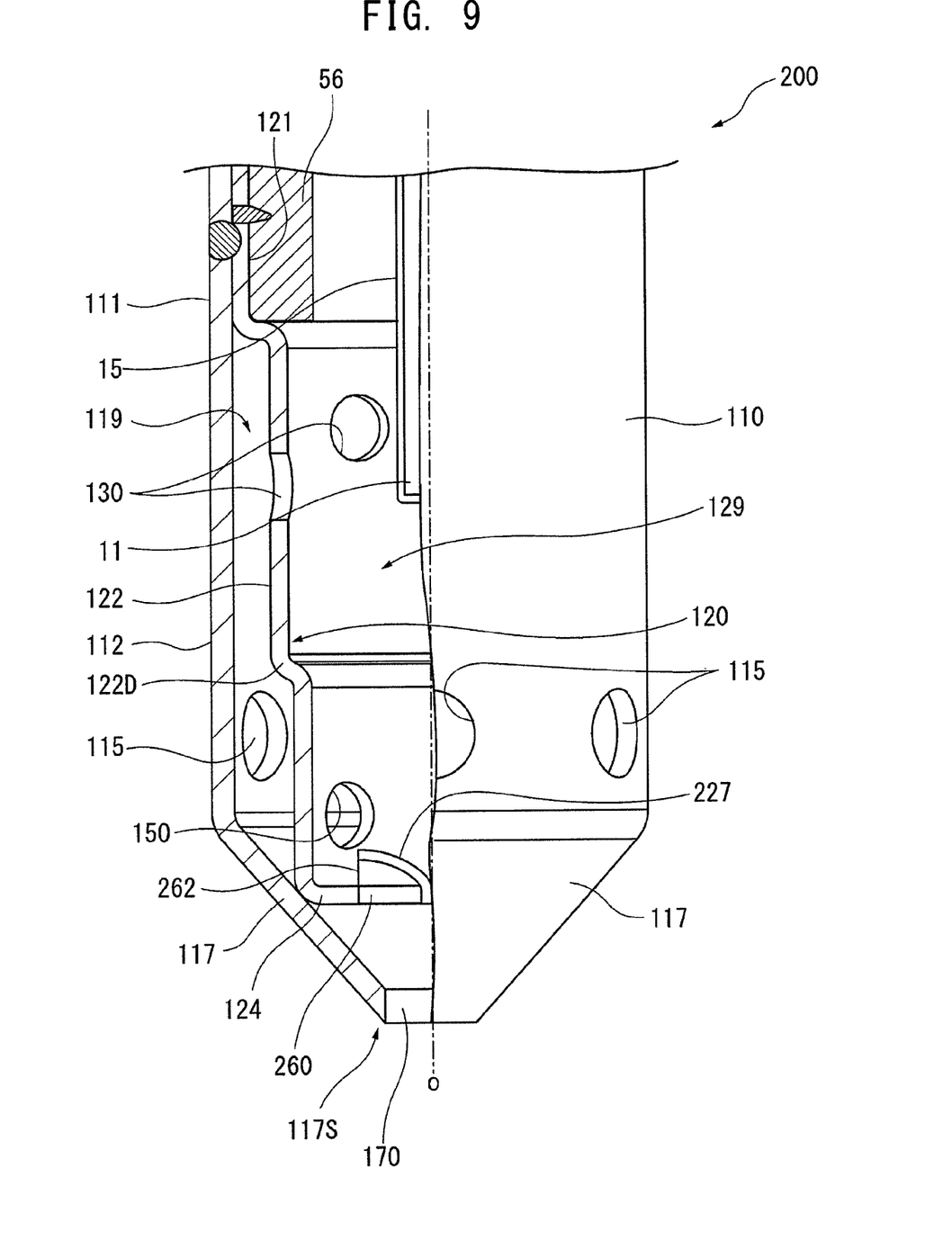
FIG. 9 Enlarged partially sectional view of a protector of a gas sensor according to a second embodiment of the present invention.
Figure 10:
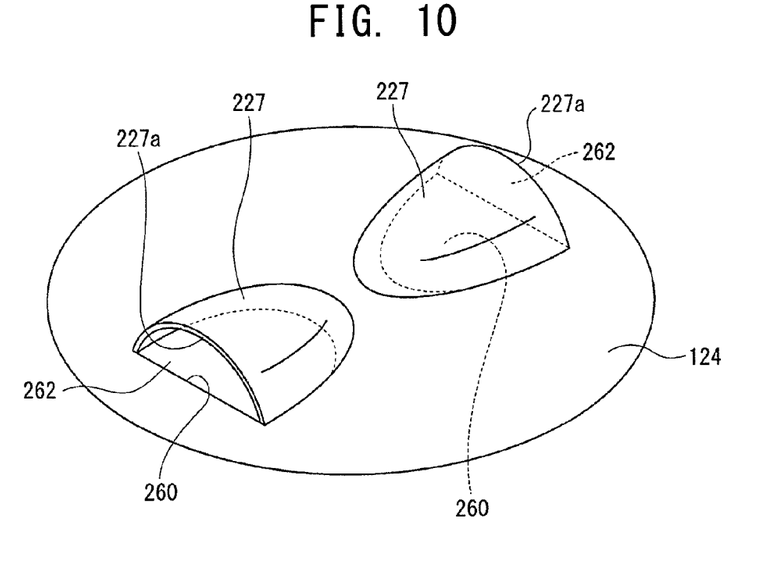
FIG. 10 Perspective view showing cover portions and bottom wall openings formed in a bottom wall of an inner protector in the second embodiment.

In FIG. 9, the bottom wall 124 of the inner protector 120 is substantially parallel to a plane perpendicular to the direction of the axis O. Two substantially semicircular portions of the bottom wall 124 are recessed rearward in such a manner as to be pressed axially inward, thereby forming the respective cover portions 227. Specifically, as shown in FIG. 10, two parallel slits 227a are formed in the bottom wall 124. Two semicircular portions of the bottom wall 124 which are located between the slits 227a and which face each other are pressed rearward, thereby forming the two cover portions 227. Each of the two cover portions 227 opens radially outward on a side toward the slit 227a (side opening 262) and assumes the form of a low-profile hemisphere. Each of the cover portions 227 and the bottom wall 124 are away from each other along the direction of the axis O at the corresponding slit 227a and are connected together at the semicircular edge of the cover portion 227. The two cover portions 227 are disposed in such a manner that their semicircular edges are in contact with each other at the center of the bottom wall 124 and that their side openings 262 are oriented in radially opposite directions.

Each of the cover portions 227 is supported by the bottom wall 124 in such a condition that a subportion of the cover portion 227 is away from the bottom wall 124 in the direction of the axis O (in such a condition that "the cover portion and the bottom wall are partially away from each other along the direction of the axis" appearing in a claim). Furthermore, side openings 262 are formed at an angle with the direction of the axis O in respective regions (associated with the slits 227a) where the cover portions 227 and the bottom wall 124 are away from each other along the direction of the axis O, and communicate with the respective bottom wall openings 260. The bottom wall openings 260 allow exhaust gas and water droplets which have been introduced into the gas detection chamber 129, to be discharged to the exterior of the inner protector 120 through the side openings 262.

In the second embodiment, since a plurality of (two) bottom wall openings 260 are provided, the total opening area of the bottom wall openings 260 becomes large; as a result, exhaust gas discharge and water drainage from the inner protector 120 can be further enhanced.

Figure 11:
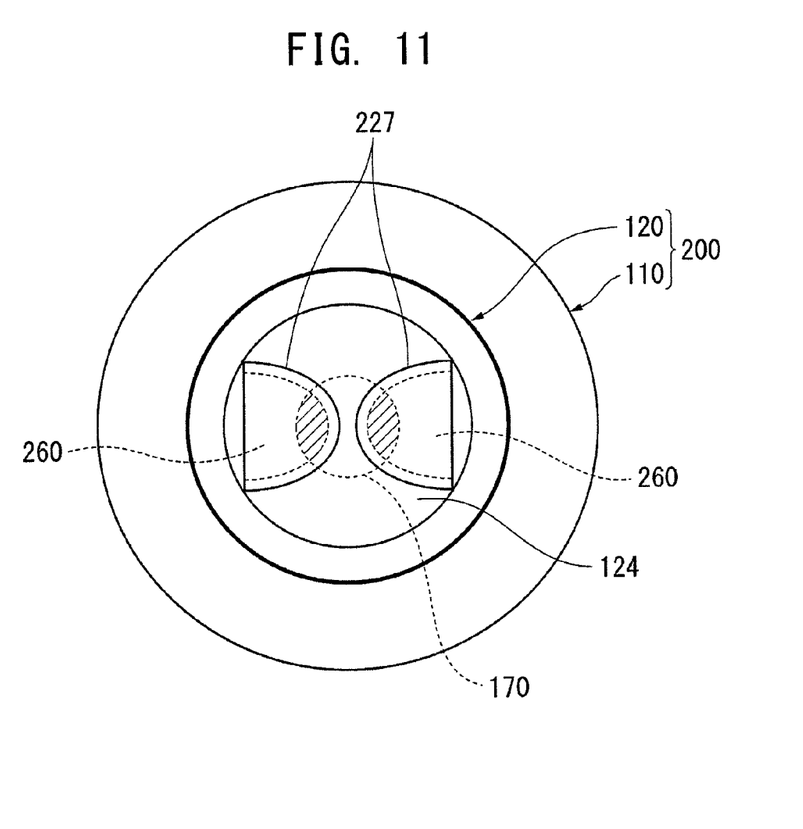
FIG. 11 Plan view showing a condition of overlapping of the bottom wall openings (cover portions) of the inner protector and an outer gas discharge hole of an outer protector as viewed frontward from the rear side of the gas sensor of the second embodiment.

FIG. 11 shows a condition of overlapping of the bottom wall openings 260 (the cover portions 227) of the inner protector 120 and the outer gas discharge hole 170 of the outer protector 110 as viewed frontward from the rear side of the gas sensor 2.

As shown in FIG. 11, the bottom wall openings 260 and the outer gas discharge hole 170 at least partially (hatched region in FIG. 11) overlap each other. Thus, by means of the bottom wall openings 260 and the outer gas discharge hole 170 being located in proximity to each other with respect to a direction perpendicular to the direction of the axis O, the gas-to-be-measured can flow from the inner protector 120 to the ambient atmosphere along the direction of the axis O. Therefore, responsiveness of the gas sensor 2 can be further improved.

In the second embodiment, also, a strong negative pressure is generated in the vicinity of the front end of the taper wall 117 on the downstream side with respect to a flow of the gas-to-be-measured, thereby intensifying the effect of sucking out exhaust gas and water droplets which have been introduced into the gas detection chamber 129, from the outer gas discharge hole 170 via the bottom wall openings 260. Therefore, responsiveness of the gas sensor 2 improves. Also, even when a water droplet or the like comes flying along the direction of the axis O into the bottom wall openings 260 through the outer gas discharge hole 170, the cover portions 227 block off the water droplet or the like. Therefore, the water droplet or the like is unlikely to directly reach the gas sensor element 10, whereby the gas sensor element 10 can be protected from adhesion of water.

The present invention is not limited to the above embodiments, but may be modified in various other forms. For example, the bottom wall opening and the cover portion of the inner protector are not limited in shape and quantity to those mentioned above. For example, the cover portion may be formed as follows: a slit resembling a squarish letter U or the letter U is formed in the bottom wall of the inner protector, and a portion of the bottom wall surrounded by the slit is pressed rearward. In this case, a single subportion of the cover portion extends in the direction of the axis while being connected to the bottom wall.

In the above embodiments, the drain hole and the inner gas introduction hole are provided on the same generatrix of the side wall of the inner protector; furthermore, the outer gas introduction hole is formed on a generatrix of the outer protector which is located on the same radial direction as that on which the generatrix of the inner protector is located. However, the holes may be formed on the respectively different generatrices, or a certain hole may be formed on a different generatrix. Also, the number of the outer gas introduction holes and the number of the inner gas introduction holes are not limited to six, and the number of the drain holes is not limited to four. Also, the size and shape of the holes may be determined arbitrarily.

Also, the present invention can be similarly applied to oxygen sensors, $NO_x$ sensors, HC sensors, temperature sensors, etc.

DESCRIPTION OF REFERENCE NUMERALS 1, 2: gas sensor
10: gas sensor element
11: detection portion
50: metallic shell
100, 200: protector
110: outer protector
112: side wall of outer protector
115: outer gas introduction hole
117: taper wall
117s: front end edge of taper wall
118: outer bottom wall
119: gap
120: inner protector
122: side wall of inner protector
122D: stepped portion of inner protector
124: bottom wall of inner protector
127, 227: cover portion
129: gas detection chamber (interior space of inner protector)
130: inner gas introduction hole
150: drain hole
160, 260: bottom wall opening
162, 262: side opening
170: outer gas discharge hole
O: axis
SL: area defined by front end edge of taper wall
S: area of opening of outer gas discharge hole
R: range

The invention claimed is:

1. A gas sensor comprising:
a gas sensor element extending in a direction of an axis and having a detection portion at its front end portion for detecting a gas-to-be-measured;
a tubular metallic shell holding the gas sensor element in such a manner as to allow the detection portion to project from its front end; and
a protector fixed to a front end portion of the metallic shell and enclosing the detection portion;
wherein the protector comprises:
an inner protector which accommodates the detection portion of the gas sensor element in its interior space and has a tubular side wall having an inner gas introduction hole for introducing the gas-to-be-measured into the interior space, and a bottom wall provided at a front end of the side wall, and
an outer protector which accommodates the inner protector therein with a gap formed between the outer protector and the side wall of the inner protector and has a tubular side wall having an outer gas introduction hole provided frontward of the inner gas introduction hole with respect to the direction of the axis and adapted to introduce the gas-to-be-measured into the gap;
the outer protector has a frustum-like taper wall tapering frontward from a front end of the side wall with respect to the direction of the axis and an outer gas discharge hole formed inside a front end edge of the taper wall and establishing communication between the interior and the exterior of the outer protector;
when SL represents an area defined by the front end edge of the taper wall, the outer gas discharge hole has an area S which satisfies a relational expression $\frac{1}{2} \times SL \leq S \leq SL$; and
the bottom wall of the inner protector has a bottom wall opening, the inner protector has a cover portion covering the bottom wall opening from a rear side with respect to the direction of the axis and recessed rearward of the bottom wall with respect to the direction of the axis, and the cover portion and the bottom wall are partially away from each other along the direction of the axis, thereby forming a side opening.

2. A gas sensor according to claim 1, wherein the bottom wall opening and the outer gas discharge hole overlap each other as viewed in the direction of the axis.

3. A gas sensor according to claim 1, wherein the side opening and the outer gas discharge hole overlap each other as viewed in the direction of the axis.

4. A gas sensor according to claim 1, wherein the side wall of the inner protector has a drain hole, and the drain hole does not overlap in position along the direction of the axis with the outer gas introduction hole and overlaps in position along the direction of the axis with the side opening.

5. A gas sensor according to claim 1, wherein the outer gas discharge hole and the side opening are in such a dimensional relation that a minimum width of the outer gas discharge hole is greater than a maximum length of the side opening along the direction of the axis.

6. A gas sensor according to claim 1, wherein the minimum width of the outer gas discharge hole is 2 mm or greater.

7. A gas sensor according to claim 1, wherein the maximum length of the side opening along the direction of the axis is 1.6 mm or greater.

8. A gas sensor according to claim 1, wherein the side wall of the inner protector has a stepped portion which has a front-oriented surface and expands radially outward along a rearward direction, and the stepped portion is located within a range along the direction of the axis between the outer gas introduction hole and the inner gas introduction hole.

9. A gas sensor according to claim 1, wherein the outer gas introduction hole is provided downstream from the inner gas introduction hole.

10. A gas sensor according to claim 1, wherein the outer gas introduction hole is provided below the inner gas introduction hole.

* * * * *